United States Patent [19]

Akhavan-Tafti et al.

[11] Patent Number: 5,686,258

[45] Date of Patent: *Nov. 11, 1997

[54] CHEMILUMINESCENT DETECTION OF HYDROLYTIC ENZYMES USING AN ACRIDAN

[75] Inventors: Hashem Akhavan-Tafti; Zahra Arghavani, both of Sterling Heights; Renuka DeSilva, Northville, all of Mich.

[73] Assignee: Lumigen, Inc., Southfield, Mich.

[*] Notice: The term of this patent shall not extend beyond the expiration date of Pat. No. 5,491,072.

[21] Appl. No.: 300,367

[22] Filed: Sep. 2, 1994

Related U.S. Application Data

[63] Continuation-in-part of Ser. No. 205,093, Mar. 2, 1994, and Ser. No. 228,290, Apr. 15, 1994, Pat. No. 5,523,212, each is a continuation-in-part of Ser. No.61,810, May 17, 1993, Pat. No. 5,491,072.

[51] Int. Cl.[6] .................................................. G01N 33/535
[52] U.S. Cl. .......................... 435/7.91; 435/6; 435/7.1; 435/7.9; 435/7.92; 435/7.93; 435/7.94; 435/7.95; 435/18; 435/28; 435/966; 435/968; 435/975
[58] Field of Search ........................... 435/26, 7.1, 7.9, 435/7.91, 7.92, 7.93, 7.94, 7.95, 28, 18, 966, 968, 975

[56] References Cited

U.S. PATENT DOCUMENTS

| | | | |
|---|---|---|---|
| 5,171,668 | 12/1992 | Sugiyama | 435/28 |
| 5,206,149 | 4/1993 | Oyama | 435/28 |
| 5,306,621 | 4/1994 | Kricka | 435/7.91 |
| 5,491,072 | 2/1996 | Akhavan-Tafti et al. | 435/28 |

OTHER PUBLICATIONS

McCapra, F., Acc. Chem. Res., 9(6), 201–8 (1976).
Obzansky, D.M., et al., Clin. Chem., 37, 1513–8 (1991).
Wigle, D.A., et al., BioTechniques, 14, 562–3 (1993).
Tsuji, A., et al., Anal. Sci., 5, 497–506 (1989).
Johannsson, A. et al., Clin. chim. Acta, 148, 119–24 (1985).
Cook, D.B. et al., Clin. Chem., 39, 965–71 (1993).
Thorpe, G. et al., in Bioluminescence and Chemiluminescence, New Perspectives, J. Scholmerich, et al, Eds., 199–208 (1987).
Ii, M. et al., Biochem. Biophys. Res. Comm., 193(2), 540–5 (1993).
Zomer, G., et al., In *Luminescence Techniques in Chemical and Biological Analysis*, W. Baeyens, et al., eds., Dekker, New York, 505–521, (1991).

Primary Examiner—Lora M. Green
Attorney, Agent, or Firm—Ian C. McLeod

[57] ABSTRACT

A chemiluminescent assay method, compositions and kits are described which use a protected phenolic enhancer compound which is deprotected by a hydrolytic enzyme and then enhances a chemiluminescent reaction. The reaction involves an acridan compound, preferably a derivative of an N-alkylacridan-9-carboxylic acid, which is activated to produce light by a peroxide compound and a peroxidase enzyme in the presence of the deprotected enhancer. The result is enhanced generation of light from the reaction. The hydrolytic enzyme is present alone or linked to a member of a specific binding pair in an immunoassay, DNA probe assay or other assay where the hydrolytic enzyme is bound to a reporter molecule.

34 Claims, 2 Drawing Sheets

CHEMILUMINESCENT DETECTION OF HYDROLYTIC ENZYMES USING AN ACRIDAN

CROSS-REFERENCE TO RELATED APPLICATION

This application is a Continuation-In-Part of application Ser. Nos. 08/205,093 filed on Mar. 2, 1994 and 08/228,290 filed Apr. 15, 1994 now U.S. Pat. No. 5,523,212 which are Continuations-In-Part of application Ser. No. 08/061,810 filed on May 17, 1993 now U.S. Pat. No. 5,491,072.

BACKGROUND OF THE INVENTION

(1) Field of the Invention

This invention relates to an improved method of generating light chemically (chemiluminescence) by the action of an enzyme which generates an agent which promotes the reactivity of a peroxidase enzyme which, in turn, catalyzes a chemiluminescent reaction. The invention also relates to the use of this method to detect the first enzyme. Further, the invention relates to the use of the method to detect and quantitate various biological molecules including haptens, antigens and antibodies by the technique of immunoassay, proteins by Western blotting, DNA and RNA by Southern and Northern blotting, respectively. The method may also be used to detect DNA in DNA sequencing applications. The method may also be used to detect DNA mutations.

(2) Description of Related Art (a) Aryl and alkyl esters of 10-methylacridan-9-carboxylic acid undergo autoxidation to N-methylacridone in dipolar aprotic solvents under strongly basic conditions to produce chemiluminescence (F. McCapra, Acc. Chem. Res., 9(6), 201–8 (1976)). Chemiluminescence quantum yields ranged from $10^{-5}$ to 0.1 and were found to increase as the $pK_a$ of the phenol or alcohol leaving group decreased. Quantum yields in aqueous solution were significantly lower due a competing non-luminescent decomposition of an intermediate. Addition of the cationic surfactant CTAB increased the apparent light yield 130-fold by preventing a competing dark reaction.

Applicants' co-pending applications Ser. Nos. 08/061,810 filed May 17, 1993 now U.S. Pat. No. 5,491,072, 08/205,093 filed on Mar. 2, 1994 and 08/228,290 filed Apr. 15, 1994 now U.S. Pat. No. 5,523,212 disclose chemiluminescent acridan compounds useful for detection of peroxidase enzymes such as horseradish peroxidase (HRP). No reports other than applicants' aforementioned co-pending applications exist on the use of peroxidase or other enzymes to oxidize acridans to produce chemiluminescence.

(b) Enzymatic Amplification Schemes

U.S. Pat. No. 5,306,621 to Kricka describes a method for the enzymatic generation of an enhancer from an inactive pro-enhancer for the HRP-catalyzed chemiluminescent oxidation of luminol. No disclosure or suggestion is made of the use of acridans as chemiluminescent substrates. The relatively poor sensitivity of this method ($10^{-16}$ mol of alkaline phosphatase) reported is insufficient for many applications.

A coupled enzyme cascade reaction for the colorimetric detection of alkaline phosphatase has been reported (D. M. Obzansky et al, Clin. Chem., 37, 1513–8 (1991)). In this scheme, alkaline phosphatase generates a substance which reacts with an inactive form of a second enzyme, converting it to its active state. The second enzyme reacts with its own substrate producing $H_2O_2$. The $H_2O_2$ is detected through a subsequent colorimetric procedure. No disclosure or suggestion of chemiluminescent detection is made.

A chemiluminescent Western blot method has been reported wherein bound HRP-antibody conjugate catalyzes a reaction leading to the deposition of a biotin-phenol conjugate on the surface of the membrane. The bound biotin is used to capture additional HRP-streptavidin conjugate. The captured enzyme was detected by luminol chemiluminescence (D. A. Wigle, N. N. Radakovic, S. L. Venance, S. C. Pang, BioTechniques, 14, 562–3 (1993)). No disclosure or suggestion is made of the use of acridans as chemiluminescent substrates.

Several bioluminescent and chemiluminescent reactions involving multiple enzymes are known (A. Tsuji, M. Maeda, H. Arakawa, Anal. Sci., 5, 497–506 (1989)). In most of these procedures, careful consideration of the mode of action reveals that, in contrast to the present invention, only one amplification step occurs. All subsequent steps merely form an electron-relay system for effecting the ultimate luminescent reaction. Only the colorimetric method based on the generation of $NADP^+$ by alkaline phosphatase is truly a dual amplification process (A. Johannsson, C. J. Stanley, C. H. Self, Clin. Chim. Acta, 148, 119–24 (1985)). A fluorimetric assay based on the same principle is also known (D. B. Cook, C. H. Self, Clin. Chem., 39, 965–71 (1993)). Neither reference teaches or suggests the use of chemiluminescence.

IN THE DRAWINGS

FIG. 1 is a graph showing the linearity of detection of alkaline phosphatase (AP) using a reagent composition of the present invention. A solution containing the protected HRP enhancer 2-naphthyl phosphate was incubated with the indicated amounts of AP. After an initial reaction period of 30 min at 37° C., 50 µL of a reagent of the present invention maintained at room temperature was added. The reagent contained 0.1 mM 2',3',6'-trifluorophenyl 3-methoxy-10-methylacridan-9-carboxylate, 1.2 mM urea peroxide, 2 mM EDTA, 0.05% TWEEN 20 and 40 pmol of HRP. Light intensity was measured at 15 min. The term S-B refers to the chemiluminescence signal (S) in RLU in the presence of AP corrected for background chemiluminescence (B) in the absence of AP. In this manner, 0.1 amol ($1\times10^{-19}$ mol) of AP was detectable.

FIG. 2 is a graph showing the linearity of detection of β-galactosidase (β-Gal) using a reagent composition of the present invention. A solution containing the protected HRP enhancer p-phenylphenol galactoside in 0.005M sodium phosphate buffer, pH 7.0 was incubated with the indicated amounts of β-Gal at room temperature. After an initial reaction period of 30, 50 µL of the detection reagent maintained at room temperature was added. The reagent contained 0.1 mM 2',3',6'-trifluorophenyl 3-methoxy-10-methylacridan-9-carboxylate, 1.2 mM urea peroxide, 2 mM EDTA, 0.05% TWEEN 20 and 40 pmol of HRP in 0.01M tris buffer, pH 8.0. Light intensity was measured at 15 min. In this manner, 0.56 amol ($5.6\times10^{-19}$ mol) of β-Gal was detectable.

OBJECTS

It is therefore an object of the present invention to provide a method using protected enhancers to generate chemiluminescence by the action of a peroxidase enzyme for the detection of hydrolytic enzymes and conjugates thereof. It is another object of the present invention to provide a method using protected enhancers to generate chemiluminescence by the action of a peroxidase enzyme for the detection of biological materials and compounds. The detection may take the form of immunoassays in solution, the detection of proteins in Western blots and DNA in Southern blots or DNA sequencing applications and other DNA hybridization assays such as the detection of mutations.

DESCRIPTION OF THE PREFERRED EMBODIMENTS

The present invention relates to a process for producing chemiluminescence which comprises reacting a protected enhancer compound with a first enzyme to generate an enhancer substance which facilitates the reaction of an acridan compound, preferably an N-alkylacridancarboxylic acid derivative, and a peroxide with a peroxidase enzyme to produce the chemiluminescence. In a preferred embodiment the first enzyme is a hydrolytic enzyme. Preferred acridan compounds have the formula:

wherein R is selected from alkyl, heteroalkyl and aralkyl groups, wherein $R_1$ to $R_8$ are selected independently from groups which allow the production of light and wherein Y is a leaving group which allows the production of light from the acridan by reaction with a peroxide and a peroxidase.

The present invention also relates to the use of this method for detecting an analyte in an assay procedure by a chemiluminescent reaction, wherein the analyte is linked to or capable of being linked directly or indirectly to the first enzyme and wherein the amount of light produced is related to the amount of the analyte. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications.

The present invention also relates to the use of this method for detecting a hydrolytic enzyme or a conjugate of a hydrolytic enzyme with a biological molecule.

The present invention also relates to an improvement in a method for detecting an analyte in an assay procedure by a chemiluminescent reaction, the improvement which comprises: providing a reagent composition which generates light in the presence of a hydrolytic enzyme. The reagent composition comprises an aqueous solution containing an N-alkylacridancarboxylic acid derivative of the formula:

a peroxide compound, a peroxidase enzyme, a protected enhancer substance which may be a phenolic compound which enhances the reactivity of the peroxidase; a surfactant which increases the light production, and a chelating agent which prevents the peroxide compound from activating the N-alkylacridancarboxylic acid derivative prior to reaction with the peroxidase.

The present invention involves a method of generating an enhancer or cycling agent by the action of a first enzyme which enhances or amplifies the action of a peroxidase enzyme which, in turn, catalyzes a chemiluminescent reaction. The invention thereby allows the use of this method to detect the first enzyme with very high sensitivity due to the two signal amplification processes. The intensity of the resulting light provides a direct measure of the quantity of labeled organic or biological molecule.

The present invention also contemplates kits for detecting any of an analyte, a hydrolytic enzyme or a hydrolytic enzyme conjugate in an assay procedure by a chemiluminescent reaction. Kits useful for practicing the present invention in any of its embodiments will comprise in one or more containers:

a) an acridan compound as described above;

b) a peroxide if the analyte to be detected is not the peroxide or a reagent which generates peroxide;

c) a peroxidase enzyme, if the analyte to be detected is not the peroxidase or a conjugate of a peroxidase with the analyte or a conjugate of a peroxidase with a reagent which forms a specific binding pair with the analyte;

d) a protected enhancer compound; and optionally e) a surfactant and a chelating agent.

Kit components may be packaged separately or in various combinations as will be apparent on consideration of the various modes of carrying out reactions of the present invention detailed below.

The reaction method of the present invention may be carried out in several different modes. In one mode or embodiment, the hydrolytic enzyme is reacted separately with an aqueous solution of the protected enhancer at a temperature from about room temperatue to at least about 40° C. The solution may contain agents such as metal ions beneficial for enzyme activity. After a suitable reaction or incubation period, this solution, or a portion thereof, is mixed with a second solution containing the acridan compound, the peroxide and the peroxidase. The second solution may optionally contain other agents including surfactants and metal-chelating agents. In another embodiment, the acridan compound is not included in the second solution, but is separately added to the final reaction solution. In a further embodiment, the protected enhancer, the acridan, the peroxide, the peroxidase and the surfactant are all included in an aqueous solution for direct reaction with the hydrolytic enzyme.

Scheme 1

-continued
Scheme 1

Removal of an X group from a protected enhancer by an enzyme generates a catalyst or enhancer, such as a phenol, which greatly enhances the ability of a peroxidase enzyme, particularly horseradish peroxidase, to catalyze the oxidation of an N-alkylacridancarboxylic acid derivative with hydrogen peroxide to produce light. A preferred class of protected enhancers comprises compounds of the formula Ar—OX wherein Ar is an aromatic group and X is a leaving group which can be cleaved by a hydrolytic enzyme to produce a phenolic compound Ar—OH or its anion. Some examples of masked or protected phenols are shown in Scheme 1 with specific leaving groups X. Examples of specific enzymes which react with suitably protected phenols by cleaving the X group and liberating the phenol include acid phosphatase, alkaline phosphatase, phosphodiesterase, phospholipase, β-D-galactosidase, β-glucuronidase, β-glucosidase, lactase, carboxyl esterase, and acetylcholinesterase. Possible O—X groups include any chemical leaving group which is stable under the conditions of use and may be cleaved by reaction with an enzyme, including without limitation alkyl or aryl carboxyl ester, inorganic oxyacid salt including phosphate and sulfate, and oxygen-pyranoside including β-D-galactoside, β-glucuronide, and β-glucoside and the like as are apparent to those of ordinary skill in the art. Phenolic compounds known to enhance other peroxidase reactions are described in G. Thorpe, L. Kricka, in *Bioluminescence and Chemiluminescence, New Perspectives*, J. Scholmerich, et al., Eds., pp. 199–208 (1987), M. Ii, H. Yoshida, Y. Aramaki, H. Masuya, T. Hada, M. Terada, M. Hatanaka, Y. Ichimori, *Biochem. Biophys. Res. Comm.*, 193(2), 540–5 (1993), and in U.S. Pat. Nos. 5,171,668 and 5,206,149 which are incorporated herein by reference. Preferred enhancers are selected from the group consisting of substituted phenols, unsubstituted and substituted naphthols, including but not limited to: p-phenylphenol, p-iodophenol, p-bromophenol, p-hydroxycinnamic acid, 2-naphthol and 6-bromo-2-naphthol.

Numerous acridan compounds are useful in the practice of the present invention. Applicants' co-pending applications Ser. Nos. 08/061,810 filed May 17, 1993, 08/205,093 filed on Mar. 2, 1994 and 08/228,290 filed Apr. 15, 1994 disclose various chemiluminescent acridan compounds including aryl esters (Y=OAr), especially halogen-substituted phenyl esters, thio esters (Y=SAr), especially, phenylthioesters and halogen-substituted phenylthioesters and aryl sulfonimides (Y=NR$_9$SO$_2$Ar). The disclosures of the three cited applications are incorporated herein by reference. Acridans with ring substitution, i.e. wherein one or more of R$_1$ through R$_8$ are an atom or group other than hydrogen are within the scope of compounds which will find use in the practice of the present invention.

Chelating agents which may be useful in the practice of the present invention include for example, polydentate cation complexing agents such as EDTA, EGTA and their salts as well as other reagents as are known in the art. It will be appreciated that metal-dependent enzymes such as alkaline phosphatase are adversely affected by chelating agents. In using the method of the present invention to detect these enzymes the use of chelating agents in the same solutions as the enzyme should be avoided. Surfactants which are useful within the present method include anionic surfactants such as sodium dodecyl sulfate (SDS), cationic surfactants such as the quaternary ammonium surfactants or preferably a nonionic surfactant such as polyoxyethylenated alkylphenols, polyoxyethylenated alcohols, polyoxyethylenated ethers, polyoxyethylenated sorbitol esters and the like.

An important aspect of the present invention is that a composition containing an N-alkylacridancarboxylic acid derivative, a peroxide, a peroxidase enzyme and a protected enhancer does not generate a large background chemiluminescent signal in the absence of the hydrolytic enzyme. Reaction with the hydrolytic enzyme to form the free enhancer causes chemiluminescence with an extended duration compared to the luminol system disclosed in U.S. Pat. No. 5,306,621. Extending the duration simplifies the measurement by obviating the need for precise reaction timing and increases the sensitivity of detection when using film-based detection methods.

Other advantages of N-alkylacridancarboxylic acid derivatives and compositions of the present invention containing compared to art-known methods is the increased sensitivity and dynamic range of detection of the first enzyme. Comparative experiments show at least a 100-fold lowering of the detection limit of alkaline phosphatase using a reagent composition of this invention compared to a reagent incorporating luminol.

These and other advantages will be apparent by consideration of the examples.

EXAMPLES

Example 1

Synthesis of p-Iodophenyl Phospate, Disodium Salt

Pyridine (0.395 g, 5 mmol) was dissolved in 15 mL of CH$_2$Cl$_2$. The solution was cooled to about 5° C. and stirred while POCl$_3$ (2.30 g, 15 mmol) was added slowly. Next, a solution of p-iodophenol (1.10 g, 5 mmol) in 10 mL of CH$_2$Cl$_2$ was added dropwise over a 5 min period. The cooling bath was removed and stirring continued for 30 min. The solvents were removed under reduced pressure and 15 mL of CH$_3$CN was added to dissolve the solids. A solution of NaOH (0.80 g, 20 mmol) in 1 mL of water was added dropwise with stirring causing a white precipitate. After standing 10 min, the solids were collected and washed with a large volume of CH$_3$CN followed by acetone and dried in the air.

Example 2

Synthesis of p-Phenylphenol Phosphate, Disodium Salt

Pyridine (0.395 g, 5 mmol) was dissolved in 15 mL of CH$_2$Cl$_2$. The solution was cooled to about 5° C. and stirred while POCl₃ (2.30 g, 15 mmol) was added slowly. Next, a solution of p-phenylphenol (0.85 g, 5 mmol) in 10 mL of $CH_2Cl_2$ was added dropwise over a 5 min period. The cooling bath was removed and stirring continued for 30 min. The solvents were removed under reduced pressure and 15 mL of $CH_3CN$ was added to dissolve the solids. A solution of NaOH (0.80 g, 20 mmol) in 1.2 mL of water was added dropwise with stirring causing a white precipitate. After standing 10 min, the solids were collected and washed with a large volume of $CH_3CN$ followed by acetone and dried in the air.

Example 3

Synthesis of p-Iodophenyl-β-D-galactopyranoside p-Iodophenol (1 g, 4.5 mmol) dissolved in 3 mL of acetone was treated with 3 mL of 5M KOH (aq). Acetobromogalactose (5.6 g, 13.6 mmol) was added in portions to the stirred solution. Initially a 4.1 g portion was added with 1 ml of 5M KOH at two-three hour intervals, 0.5 g portions of acetobromogalactose was added accompanied by 0.5 ml of 5M KOH until a total of 5.6 g (3 eq.) was added. Stirring was continued overnight. Water was added and the solution extracted with methylene chloride followed by ethyl acetate. The combined organic layers were evaporated and the crude product purified by column chromatography on silica using 30% ethyl acetate in hexane to remove unreacted sugar. Removal of solvents from the appropriate fractions produced the tetraacetate ester of the desired compound. Hydrolysis to the desired compound was achieved by dissolving a 300 mg portion in 2 mL of acetone and stirring with 650 μL of 10M KOH overnight. The acetone was evaporated and 30 mL of water added. Ammonium chloride was added to neutralize the pH and the resulting solution extracted with ethyl acetate. The ethyl acetate solution was dried with $MgSO_4$ and concentrated under reduced pressure to obtain a white solid which was further purified by column chromatography using 50% methanol/ethyl acetate; ¹H NMR (CD₃OD) δ3.28–3.89 (m, 6H), 4.81 (d, 1H), 6.89–7.57 (m,4H).

Example 4

Synthesis of p-Phenylphenol-β-D-galactopyranoside

To a solution of p-phenylphenol (250 mg, 1.46 mmol) in acetone, 1 mL of 10N KOH was added followed by acetobromogalactose (1.8 g, 4.37 mmol). The reaction mixture was stirred overnight at room temperature. TLC analysis showed no starting material left. 10N KOH (1 mL) was added to complete deacetylation and the solution was again stirred overnight. After evaporation of acetone, the crude material was taken up in ethyl acetate and washed with 5×150 mL of water. Ethyl acetate was dried with $MgSO_4$ and concentrated under reduced pressure to obtain a white solid which was further purified by column chromatography using 30% methanol/ethyl acetate; ¹H NMR (CD₃OD) δ3.56–3.91 (m, 6H), 4.89 (m, 1H), 7.15–7.57 (m,9H).

Example 5

Synthesis of p-Phenylphenol Acetate

Pyridine (2 mL) was dissolved in 15 mL of $CH_2Cl_2$. The solution was cooled to about 5° C. and stirred while while acetyl chloride (393 mg, 5 mmol) was added slowly. Next, a suspension of p-phenylphenol (0.85 g, 5 mmol) in 20 mL of $CH_2Cl_2$ was added dropwise over a 15 min period. The cooling bath was removed and stirring continued for 30 min. The solvents were removed under reduced pressure and 50 mL of ethyl acetate was added to dissolve the solids. The solution was extracted with water, dried over $Na_2SO_4$ and evaporated under reduced pressure.

Example 6

Synthesis of Peroxidase Substrate Compound

2',3',6'-Trifluorophenyl 3-Methoxy-10-methylacridan-9-carboxylate (a) The compound 3-methoxyacridine-9-carboxylic acid was prepared by a method described in the literature (G. Zomer, J. Stavenuiter, R. Van Den Berg, E. Jansen, In *Luminescence Techniques in Chemical and Biochemical Analysis*, W. Baeyens, D. De Keukeleire, K. Korkidis, eds., Dekker, New York, 505–521, (1991)). Condensation of the commercially available (Aldrich) 3-methoxydiphenylamine with oxalyl chloride produced a mixture of the 3-methoxy and 1-methoxyacridinecarboxylic acids which were conversion to the esters as a mixture.

(b) A mixture of the 3-methoxy and 1-methoxyacridinecarboxylic acids (1.5 g) was suspended in 10 mL of $SOCl_2$ and the reaction mixture was refluxed for 3 h. The solvent was removed under reduced pressure to obtain a yellow solid which was dissolved in methylene chloride ($CH_2Cl_2$) and pyridine (0.7 mL) under argon. A solution of 2,3,6-trifluorophenol (0.878 g) in $CH_2Cl_2$ was added dropwise. The solution was stirred overnight at room temperature then diluted with more $CH_2Cl_2$ (100 mL) and washed with water (3×50 mL). The organic layer was dried over $Na_2SO_4$ and concentrated to obtain a mixture of isomeric esters. The product 2',3',6'-trifluorophenyl 3-methoxyacridine-9-carboxylate was isolated by chromatography on silica with 25% ethyl acetate/hexane: ¹H NMR (CDCl₃) δ4.043 (s, 3H),7.08–8.25 (m, 9H).

(c) The previous compound (0.24 g) was dissolved in methylene chloride (3 mL) under argon and methyl trifluoromethanesulfonate (0.1 mL, 1.4 eq.) was added. The solution was stirred overnight at room temperature to yield a thick yellow precipitate. This precipitate was filtered, washed with ether and dried to obtain pure 2',3',6'-trifluorophenyl 3-methoxyacridinium-9-carboxylate trifluoromethanesulfonate as yellow crystals: ¹H NMR (DMSO-d₆) δ4.288 (s, 3H), 4.837 (s, 3H), 7.64–8.89 (m, 9H).

(d) The acridinium ester (35 mg) was suspended in absolute ethanol (15 mL) and solution was refluxed for 10 min to obtain a clear solution. Excess ammonium chloride (4 g) was added by portions to the solution followed by zinc (4 g) causing immediate decolorization of the solution. The colorless solution was refluxed for 30 min, cooled, filtered and the precipitate washed with ethanol (3×20 mL). The solution was concentrated to obtain an off-white solid which was redissolved in methylene chloride and washed with water (3×50 mL). Crude material obtained after evaporation of methylene chloride was chromatographed on silica gel (ethyl acetate/hexane) to yield the pure acridan 2',3',6'-trifluorophenyl 3-methoxy-10-methylacridan-9-carboxylate as a white solid: ¹H NMR (CDCl₃) δ3.422 (s, 3H), 3.847 (s, 3H), 5.25 (s, 1H), 6.54–7.39 (m, 9H).

Example 7

Synthesis of Peroxidase Substrate Compound

2',3',6'-Trifluorophenyl Acridine-9-carboxylate (a) Acridine-9-carboxylic acid (Aldrich, 0.5 g) was suspended in excess thionyl chloride (5 mL) and the reaction mixture was refluxed for 3 h. The solvent was removed under reduced pressure to obtain a yellow solid which was dissolved in methylene chloride and pyridine (0.53 g) under argon. A solution of the phenol (0.365 g) in methylene chloride was added dropwise. The solution was stirred overnight at room temperature then diluted with more methylene chloride (100 mL) and washed with water (3×50 mL). The organic layer was dried over $Na_2SO_4$ and concentrated to obtain the product. The yellow solid was further washed with ether to remove excess of phenol (82% yield): $^1H$ NMR ($CDCl_3$) δ7.08–7.28 (m, 2H) 7.71–8.42 (m, 8H).

(b) 2',3',6'-Trifluorophenyl 10-methylacridinium-9-carboxylate trifluoromethanesulfonate. The ester (0.30 g) was then suspended in methylene chloride (25 mL) under argon and methyl trifluoromethanesulfonate (0.95 mL) was added. The solution was stirred overnight at room temperature to yield a thick yellow precipitate. This precipitate was filtered, washed with ether and dried to obtain the product as yellow crystals. $^1H$ NMR (acetone-$d_6$) δ5.29 (s, 3H), 7.50–7.67 (m, 2H), 8.26–9.14 (m, 8H).

(c) 2',3',6'-Trifluorophenyl 10-methylacridan-9-carboxylate. The acridinium ester (0.20 g) was dissolved in 10 mL of glacial acetic acid to obtain a yellow solution and zinc was added (2.5 g) causing immediate decolorization of the solution. After 5 min stirring at room temperature, TLC of the reaction mixture showed a nonpolar material. The acetic acid was decanted and the solid washed with methylene chloride. The combined organic solutions were evaporated to obtain a crude solid which was redissolved in methylene chloride and washed with 2 or 3—50 mL portions of water. The crude material obtained after evaporation of methylene chloride was chromatographed on silica gel (20–30% ethyl acetate/hexane) to yield the pure product as a white solid. $^1H$ NMR ($CDCl_3$) δ3.44 (s, 3H), 5.29 (s, 1H), 6.76–6.84 (m, 2 H) 6.99–7.39 (m, 8H).

Example 8

Detection of Alkaline Phosphatase on Membrane

A reagent was prepared for chemiluminescent detection of alkaline phosphatase conjugates on membranes in one step. The reagent which can be used for chemiluminescent Western blotting contained the protected HRP enhancer 2-naphthyl phosphate (Aldrich) at 1 mM, 0.05 mM 2',3',6'-trifluorophenyl 10-methylacridan-9-carboxylate, 2.5 mM urea peroxide, 0.5% TWEEN 20 and 40 pmol of HRP in 0.01M tris buffer, pH 8.8. In a Western blot, alkaline phosphatase-labeled antibody immobilized on nitrocellulose or PVDF membrane is detected by wetting the membrane with the detection reagent placed in a holder (transparency film) and the membrane exposed to X-ray film for a period ranging between 5 sec and 30 min and then developed.

Example 9

Linearity of Detection of Alkaline Phosphatase

Figure 1:
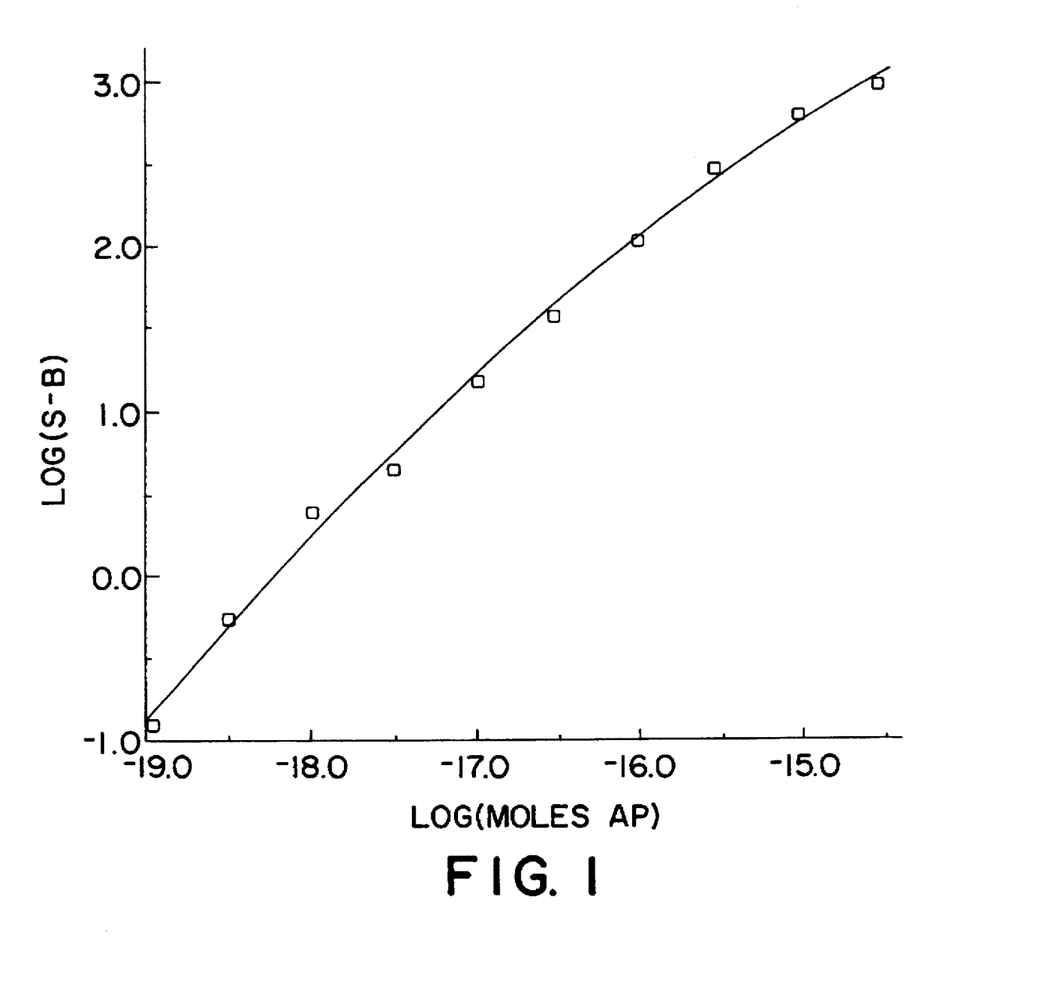

The linearity of detection of alkaline phosphatase (AP) was determined using a reagent composition of the present invention. A solution (50 µL) containing the protected HRP enhancer 2-naphthyl phosphate (1 mM) in 0.01M tris buffer, pH 8.8 was incubated with AP containing between 3.7×10$^-$15 and 1.1×10$^{-19}$ mol of enzyme. After an initial reaction period of 30 min at 37° C., 50 µL of a reagent of the present invention was added to each of these solutions. The reagent contained 0.1 mM 2',3',6'-trifluorophenyl 3-methoxy-10-methylacridan-9-carboxylate, 1.2 mM urea peroxide, 2 mM EDTA, 0.05% TWEEN 20 and 40 pmol of HRP in 0.01M tris buffer, pH 8.0. Light intensity was continuously monitored for 15 min. Reported values were measured at 15 min. FIG. 1 illustrates the excellent sensitivity obtainable; 0.11 amol (1.1×10$^{-19}$ mol) of AP was detectable. In the plot, the term S-B refers to the chemiluminescence signal (S) in RLU in the presence of AP corrected for background chemiluminescence (B) in the absence of AP. Results are the average of triplicate samples.

Example 10

Linearity of Detection of β-Galactosidase

Figure 2:
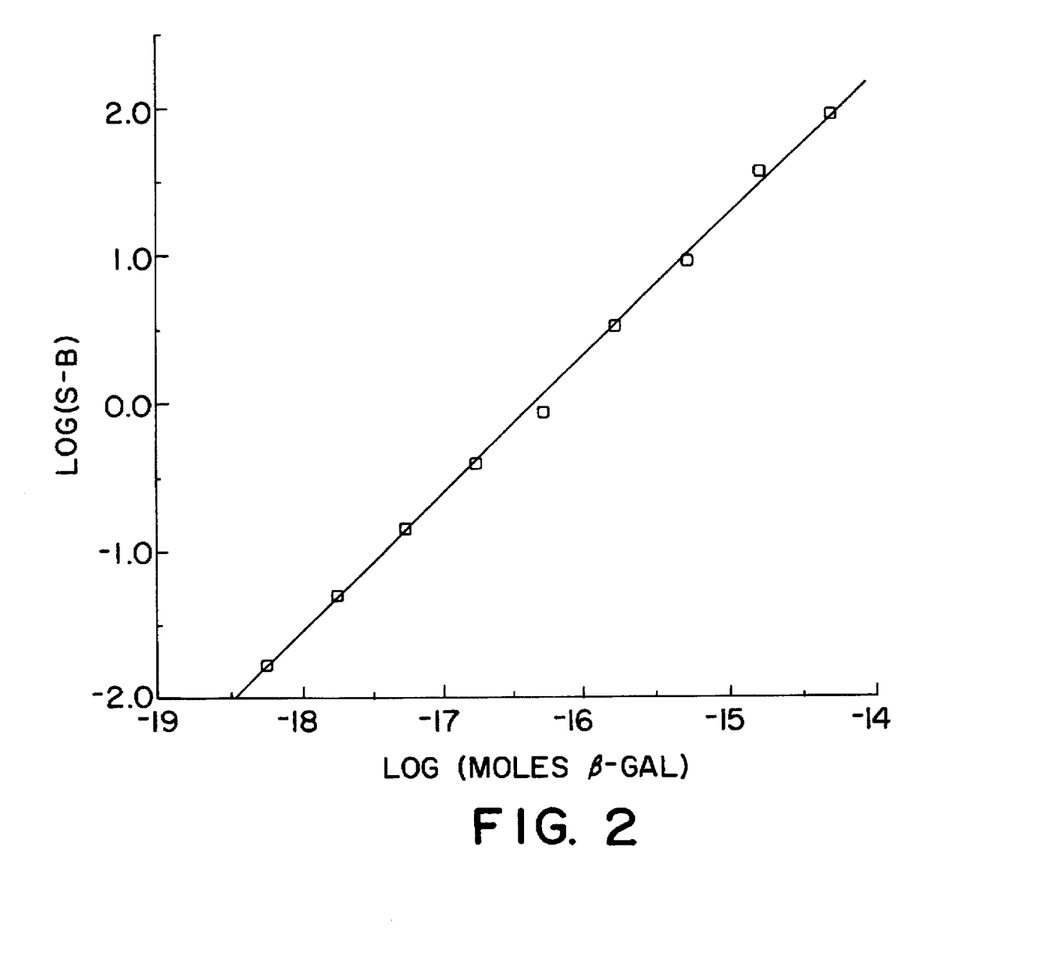

The linearity of detection of β-galactosidase (β-gal) was determined using a reagent composition of the present invention. A solution (50 µL) containing the protected HRP enhancer p-phenylphenol galactoside (0.15 mM) in 0.005M sodium phosphate buffer, pH 7.0 was incubated with β-gal containing between 5.6×10$^{-15}$ and 1.9×10$^{-19}$ mol of enzyme. After an initial reaction period of 30 min at 25° C., 50 µL of the reagent of example 9 was added to each of these solutions. FIG. 2 illustrates the excellent sensitivity obtainable; 0.56 amol (5.6×10 −19 mol) of β-galactosidase was detectable. Results are the average of triplicate samples.

It is intended that the foregoing description be only illustrative of the present invention and that the present invention be limited only by the appended claims.

We claim:

1. A method for producing chemiluminescence comprising reacting a hydrolytic enzyme with a protected enhancer, a peroxide compound, a peroxidase enzyme and an acridan compound to produce chemiluminescence; wherein the acridan has the formula:

wherein R is an alkyl, heteroalkyl or aralkyl group, wherein $R_1$ to $R_8$ are selected independently from groups which allow the production of chemiluminescence and wherein Y is a leaving group; and wherein the protected enhancer compound has the formula ArOX wherein X is a leaving group and Ar is selected from the group consisting of a substituted phenyl, a napthyl and a substituted napthyl group, wherein the hydrolytic enzyme reacts with the protected enhancer compound to remove X, thus enhancing the level of chemiluminescence produced by the acridan compound upon reaction with the peroxidase and the peroxide as compared to the level of chemiluminescence produced in the absence of the enhancer compound.

2. The method of claim 1 wherein the hydrolytic enzyme is reacted with the protected enhancer in an aqueous solution for a period of time before addition of a solution comprising the acridan, the peroxide compound and the peroxidase to produce chemiluminescence.

3. The method of claim 1 wherein the group Y is selected from the group consisting of an aryloxy group, a substituted aryloxy group, an arylthio group, a substituted arylthio group and a sulfonimide group.

4. The method of claim 1 wherein the group Y is the substituted aryloxy group.

5. The method of claim 4 wherein the substituted aryloxy group is a halogen-substituted phenoxy group.

6. The method of claim 1 wherein at least one of $R_1$ to $R_8$ is a $C_1$–$C_{20}$ alkoxy group and wherein R is a $C_1$–$C_{20}$ alkyl group.

7. The method of claim 1 wherein the acridan is 2',3',6'-trifluorophenyl 3-methoxy-10-methylacridan-9-carboxylate.

8. The method of claim 1 wherein the hydrolytic enzyme is attached to a member of a specific binding pair selected from the group consisting of a hapten, an antigen, an antibody, a protein, an oligonucleotide and a nucleic acid.

9. A method of detecting the presence or amount of a hydrolytic enzyme in a sample wherein the hydrolytic enzyme may be present in the sample in free form or as a conjugate to a biological molecule comprising:

(a) reacting the hydrolytic enzyme in the sample with a protected enhancer, a peroxide compound, a peroxidase enzyme and an acridan compound to produce chemiluminescence; wherein the acridan has the formula:

wherein R is an alkyl, heteroalkyl or aralkyl group, wherein $R_1$ to $R_8$ are selected independently from groups which allow the production of chemiluminescence and wherein Y is a leaving group; and wherein the protected enhancer compound has the formula ArOX wherein X is a leaving group and Ar is selected from the group consisting of a substituted phenyl, a napthyl and a substituted napthyl group, wherein the hydrolytic enzyme reacts with the protected enhancer compound to remove X, thus enhancing the level of chemiluminescence produced by the acridan compound upon reaction with the peroxidase and the peroxide as compared to the level of chemiluminescence produced in the absence of the enhancer compound; and (b) measuring the amount of chemiluminescence produced and relating it to the presence or amount of the hydrolytic enzyme in the sample.

10. The method of claim 9 wherein the group Y is selected from the group consisting of an aryloxy group, a substituted aryloxy group, an arylthio group, a substituted arylthio group and a sulfonimide group.

11. The method of claim 9 wherein the group Y is an substituted aryloxy group.

12. The method of claim 11 wherein the substituted aryloxy group is a halogen-substituted phenoxy group.

13. The method of claim 9 wherein at least one of $R_1$ to $R_8$ is a $C_1$–$C_{20}$ alkoxy group and wherein R is a $C_1$–$C_{20}$ alkyl group.

14. The method of claim 9 wherein the acridan is 2',3', 6'-trifluorophenyl 3-methoxy-10-methylacridan-9-carboxylate.

15. The method of claim 9 wherein the analyte is the hydrolytic enzyme.

16. The method of claim 9 wherein the hydrolytic enzyme is attached to a member of a specific binding pair selected from the group consisting of a hapten, an antigen, an antibody, a protein, an oligonucleotide and a nucleic acid.

17. A kit for detecting the presence or amount of a hydrolytic enzyme in a sample wherein the hydrolytic enzyme may be present in the sample in free form or as a conjugate to a biological molecule comprising providing in one or more containers:

(a) an acridan compound having the formula:

wherein R is an alkyl, heteroalkyl or aralkyl group, wherein $R_1$ to $R_8$ are selected independently from groups which allow the production of chemiluminescence and wherein Y is a leaving group;

(b) a peroxide compound;

(c) a protected enhancer compound of the formula ArOX, wherein X is a leaving group and Ar is selected from the group consisting of a substituted phenyl, a napthyl and a substituted napthyl group, wherein the hydrolytic enzyme reacts with the protected enhancer compound to remove X, thus enhancing the level of chemiluminescence produced by the acridan compound upon reaction with the peroxidase and the peroxide as compared to the level of chemiluminescence produced in the absence of the enhancer compound; and (d) a peroxidase enzyme.

18. The kit of claim 12 wherein the group Y is selected from the group consisting of an aryloxy group, a substituted aryloxy group, an arylthio group, a substituted arylthio group and a sulfonimide group.

19. The kit of claim 17 wherein the group Y is an substituted aryloxy group.

20. The kit of claim 19 wherein the substituted aryloxy group is a halogen-substituted phenoxy group.

21. The kit of claim 17 wherein at least one of $R_1$ to $R_8$ is a $C_1$–$C_{20}$ alkoxy group and wherein R is a $C_1$–$C_{20}$ alkyl group.

22. The kit of claim 17 wherein the acridan is 2',3',6'-trifluorophenyl 3-methoxy-10-methylacridan-9-carboxylate.

23. A kit for detecting the presence or amount of a hydrolytic enzyme in a sample wherein the hydrolytic enzyme may be present in the sample in free form or as a conjugate to a biological molecule comprising:

a reagent composition which generates chemiluminescence in the presence of a hydrolytic enzyme, said reagent composition comprising, in an aqueous solution, a protected enhancer, a peroxide compound, a peroxidase enzyme and an acridan compound which generates chemiluminescence upon reaction with the peroxide compound and the peroxidase enzyme, wherein the acridan has the formula:

wherein R is an alkyl, heteroalkyl or aralkyl group, wherein $R_1$ to $R_8$ are selected independently from groups which allow the production of chemiluminescence and wherein Y is a leaving group; and wherein the protected enhancer compound has the formula ArOX wherein X is a leaving group and Ar is selected from the group consisting of a substituted phenyl, a napthyl and a substituted napthyl group, wherein the hydrolytic enzyme reacts with the protected enhancer compound to remove X, thus enhancing the level of chemiluminescence produced by the acridan compound upon reaction with the peroxidase and the peroxide as compared to the level of chemiluminescence produced in the absence of the enhancer compound.

24. The kit of claim 23 wherein the group Y is selected from the group consisting of an aryloxy group, a substituted aryloxy group, an arylthio group, a substituted arylthio group and a sulfonimide group.

25. The kit of claim 23 wherein the group Y is an substituted aryloxy group.

26. The kit of claim 25 wherein the substituted aryloxy group is a halogen-substituted phenoxy group.

27. The kit of claim 23 wherein at least one of $R_1$ to $R_8$ is a $C_1$–$C_{20}$ alkoxy group and wherein R is a $C_1$–$C_{20}$ alkyl group.

28. The kit of claim 23 wherein the acridan is 2',3',6'-trifluorophenyl 3-methoxy-10-methylacridan-9-carboxylate.

29. A composition which generates chemiluminescence in the presence of a hydrolytic enzyme which comprises in an aqueous solution:

(a) a peroxide compound;

(b) a peroxidase enzyme;

(c) an acridan compound which generates light chemiluminescence upon reaction with the peroxide compound and the peroxidase enzyme, wherein the acridan has the formula:

wherein R is an alkyl, heteroalkyl or aralkyl group, wherein $R_1$ to $R_8$ are selected independently from groups which allow the production of chemiluminescence and wherein Y is a leaving group; and (d) a protected enhancer compound of the formula ArOX, wherein X is a leaving group and Ar is selected from the group consisting of a substituted phenyl, a napthyl and a substituted napthyl group, wherein the hydrolytic enzyme reacts with the protected enhancer compound to remove X, thus enhancing the level of chemiluminescence produced by the acridan compound upon reaction with the peroxidase and the peroxide as compared to the level of chemiluminescence produced in the absence of the enhancer compound.

30. The composition of claim 29 wherein the group Y is selected from the group consisting of an aryloxy group, a substituted aryloxy group, an arylthio group, a substituted arylthio group and a sulfonimide group.

31. The composition of claim 29 wherein the group Y is an substituted aryloxy group.

32. The composition of claim 31 wherein the substituted aryloxy group is a halogen-substituted phenoxy group.

33. The composition of claim 29 wherein at least one of $R_1$ to $R_8$ is a $C_1$–$C_{20}$ alkoxy group and wherein R is a $C_1$–$C_{20}$ alkyl group.

34. The composition of claim 29 wherein the acridan is 2',3',6'-trifluorophenyl 3-methoxy-10-methylacridan-9-carboxylate.

* * * * *

UNITED STATES PATENT AND TRADEMARK OFFICE
CERTIFICATE OF CORRECTION

PATENT NO. : 5,686,258
DATED : November 11, 1997
INVENTOR(S) : Hashem Akhavan-Tafti, Zahra Arghavani and Renuka DeSilva It is certified that error appears in the above-identified patent and that said Letters Patent is hereby corrected as shown below:

On the title page, item "[56] References Cited, "Zomer et al. Biological Analysis" should be --Biochemical Analysis--.

Column 7, line 64, delete "while", second occurrence.

Column 10, line 23, "(5.6 x 10-19 mol)" should be --(5.6 x $10^{-19}$ mol)--.

Column 12, line 31 (Claim 18), "kit of Claim 12" should be --kit of Claim 17--.

Signed and Sealed this

Fifth Day of May, 1998

*Attest:*

*Attesting Officer*

BRUCE LEHMAN

*Commissioner of Patents and Trademarks*